United States Patent [19]
Gupta

[11] Patent Number: 6,068,198
[45] Date of Patent: May 30, 2000

[54] AEROSOL GENERATING AND DISPENSING SYSTEM

[76] Inventor: Umesh Gupta, 137 Countrywood Cir., Clinton, Miss. 39056

[21] Appl. No.: 09/274,705

[22] Filed: Mar. 23, 1999

[51] Int. Cl.$^7$ ................................................ B05B 17/00
[52] U.S. Cl. ........................ 239/1; 239/324; 239/332; 141/27; 222/333; 92/98 D
[58] Field of Search ........................... 239/1, 320, 324, 239/329, 330, 331, 332; 222/333, 390, 386, 386.5; 141/2, 3, 25–27; 92/98 D, 136; 417/415, 416; 128/205.14, 205.16, 205.18

[56] References Cited

U.S. PATENT DOCUMENTS

| | | | |
|---|---|---|---|
| 4,424,738 | 1/1984 | Leighton | 92/86 |
| 5,253,981 | 10/1993 | Yang et al. | 417/3 |
| 5,292,036 | 3/1994 | Thome | 239/324 |
| 5,547,131 | 8/1996 | Brace | 239/324 |
| 5,960,693 | 1/1984 | Yuda, Jr. | 92/136 |

*Primary Examiner*—Andres Kashnikow
*Assistant Examiner*—Lisa Ann Douglas
*Attorney, Agent, or Firm*—Carl C. Kling

[57] ABSTRACT

A generator/dispenser for mono-dispersed aerosol, with droplet size precisely controlled by a stepper motor and a nozzle array having a great number of operational micro-vias, and with fluid volume dosage control. A specified dose is delivered over an accurately controlled interval of time, by decrementing the volume of a fluid reservoir upon each of a specified number of control pulses to a stepper motor, which moves a ball screw linear actuator with great precision on each control pulse. The reservoir is closed at the aerosol delivery position by a nozzle array, which is a thin sheet with myriad micro-via holes. The micro-vias are of the same dimensions and orientation, producing for a medical inhaler the desired micro-droplet volume, for example the volume of a 3-$\mu$m diameter droplet from each micro-via, for each pulse. The step sizes of the micro-stepper are selected so that, upon each pulse to the micro-stepper, the linear actuator diminishes the volume of the reservoir just enough to drive one droplet each through the operational micro-vias. The system is compact and simple in design, and can be refilled after use by dipping the fill valve end in the liquid and reversing the linear actuator. The aerosol nozzle array can easily be replaced, either separately or as a part of an integral demountable reservoir housing.

7 Claims, 3 Drawing Sheets

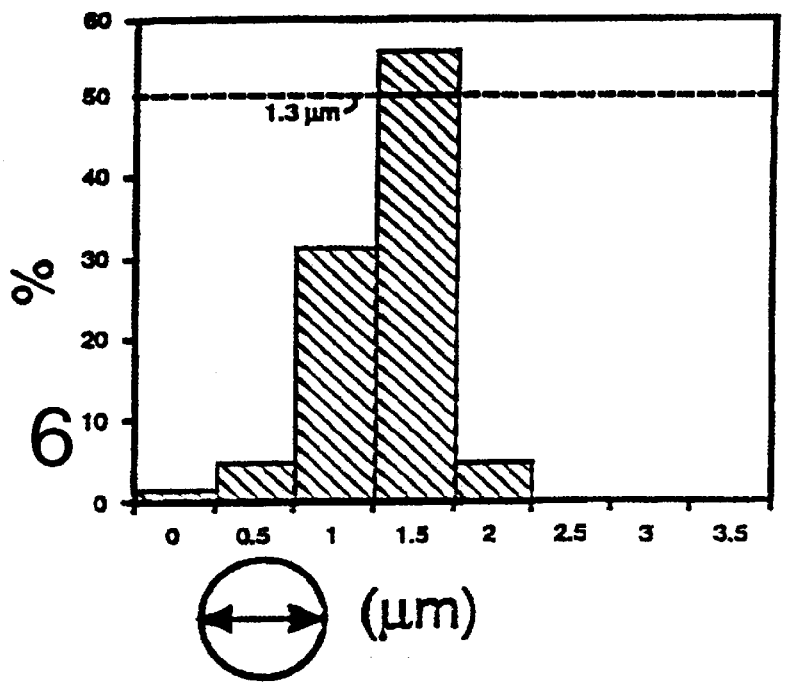
FIG. 6
FIG. 7
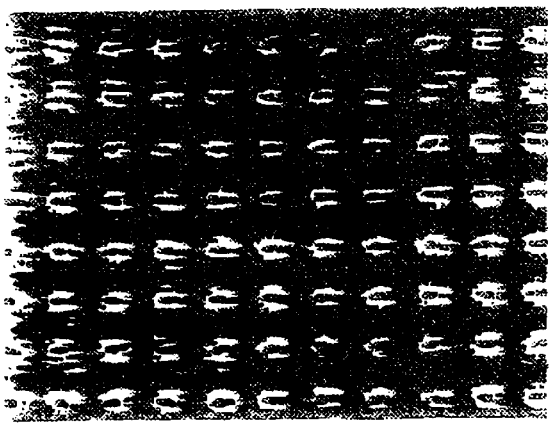
FIG. 8
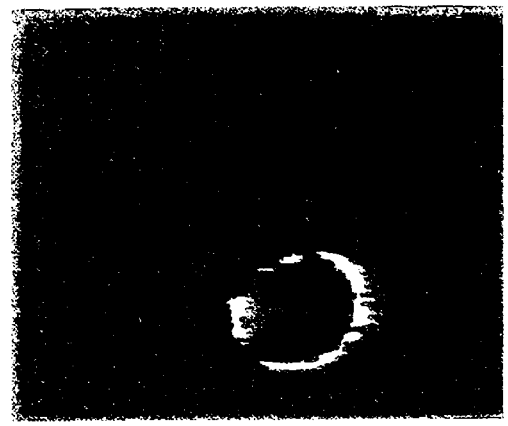

AEROSOL GENERATING AND DISPENSING SYSTEM

CROSS-REFERENCE TO RELATED APPLICATIONS (NOT APPLICABLE)

STATEMENT REGARDING FEDERALLY SPONSORED RESEARCH OR DEVELOPMENT (NOT APPLICABLE)

REFERENCE TO A MICROFICHE APPENDIX (NOT APPLICABLE)

BACKGROUND OF THE INVENTION (1) Field of the Invention

This invention relates to a monodispersed-aerosol generating and dispensing system, and more particularly relates to an aerosol system which generates a measured dose of droplets of uniform size as desired for applications such as pulmonary drug delivery, combustion efficiency enhancement, and surface coating.

(2) Description of Related Art

When aerosols are used in medicine, agriculture, or industry, it is highly desirable for the particle-size distribution to be extremely narrow. These monodispersed aerosols are important because the properties of an aerosol, such as how it is transported to receiving surfaces (such as a human lung) are typically optimized at a particular particlesize. Thus if an aerosol were comprised of particulates of only the optimum size, aerosol delivery and absorption would be extremely efficient. There is a known desire for a monodispersed-aerosol generator which is accurate, dependable and inexpensive.

U.S. Pat. No. 5,738,728, T. Tisone, issued Apr. 14, 1998, PRECISION METERED AEROSOL DISPENSING APPARATUS, for example, shows an aerosol dispensing apparatus including a positive displacement syringe pump in series with an air brush dispenser. The pump is controlled by a stepper motor. The air brush dispenser mixes the reagent with pressurized air to atomize the reagent and produce an aerosol spray.

REFERENCES

1. D. Edwards, Science, 276 (1990), pp. 1868–1871.
2. See for example, "A look at barrier packs," Spray Technology and Marketing, p. Apr. 28, 1997.
3. S. Farr, J. Schuster, P. Lloyd, L. Lloyd, J. Okikawa, and R. Rubsamen, *Respiratory Drug Delivery V*, Proceedings of the 5th International Symposium at Virginia Commonwealth University School of Pharmacy, 1995, pp. 175–185.
4. U.S. Pat. No. 5,305,018, issued Apr. 19, 1994, C. Shantz et al., "EXCIMER LASER ABLATED COMPONENTS FOR INKJET PRINTHEAD."
5. U.S. Pat. No. 5,417,897, issued May 23, 1995, S. Asakawa et al., "METHOD FOR FORMING TAPERED INKJET NOZZLES."
6. Allowed U.S. patent application 08/794,217, filed Jan. 29, 1997, K. Jain et al., "HIGH SPEED DRILLING SYSTEM FOR MICRO-VIA PATTERN FORMATION, AND RESULTING STRUCTURE."
7. See for example, U.S. Pat. No. 5,539,175, issued Jul. 23, 1996, A. Smith, et al., "APPARATUS AND PROCESS FOR OPTICALLY ABLATED OPENINGS HAVING DESIGNED PROFILE."
8. F. Jin, PhD. Thesis, University of Central Florida, 1995.
9. R. Cook, D. Malkus, and M. Plesha, *Concepts and Applications of Finite Element Analysis*, John Wiley and Sons, Inc., 1989.
10. G. Sem, TSI Quarterly, 10, 3(1984).
11. U.S. Pat. No. 5,738,728, T. Tisone, issued Apr. 14, 1998, PRECISION METERED AEROSOL DISPENSING APPARATUS.

BRIEF SUMMARY OF THE INVENTION

It is the object of the invention to provide a monodispersed-aerosol generator/dispenser which is precise in dosage and has an extremely narrow particle size distribution.

Another object of the invention is to provide an aerosol dispenser which is simple in design and adaptable to large-scale production.

A feature of the invention is the provision of a nozzle array having myriad matched micro-via-holes for forming matched micro-droplets.

Another feature of the invention is the use of a micro-stepper motor and ball screw with a rolling diaphragm to provide dosage metering, together with a nozzle array to provide identical droplet configuration for each of a myriad of droplets for each micro-step.

Still another feature of the invention is a remountable nozzle housing subassembly with integral nozzle array having myriad matched via-holes for forming the micro-droplets.

A more specific feature of the invention is the control of stepper motor and ball screw to provide a volumetric unit of liquid equal, for each micro-step of the micro-stepper motor, to one droplet from each of the myriad micro-vias of the nozzle array.

An advantage of the invention is that the stepper motor provides a set of micro-droplets for each step, one droplet for each micro-via of the nozzle array for each step of the micro-stepper, thus insuring precise metering of liquid delivered in aerosol form.

Another advantage of the invention is that the device can be simply altered— for a variety of aerosol droplet sizes by changing the nozzle array and/or by changing the step size of the stepper motor;

for a different volumetric dosage by altering the number of impulses sent to the stepper motor; and for a different number of doses between refills by changing the size of the chamber that holds the liquid.

Still another advantage of the invention is that it requires no pressurized air in generating the aerosol, and is not prone to ingesting and entraining air.

Other objects, features and advantages of the invention will be apparent from the following written description, claims, abstract and the annexed drawings.

BRIEF DESCRIPTION OF THE SEVERAL VIEWS OF THE DRAWING

FIG. 6 is a histogram showing the distribution of exit hole diameters in a nozzle array made according to a previous, commonly assigned, patent application.

FIG. 7 is a photomicrograph of a nozzle array, made according to a previous, commonly assigned, patent application.

FIG. 8 is an enlarged photomicrograph of a single micro-via-hole.

DETAILED DESCRIPTION OF THE INVENTION

Figure 1:
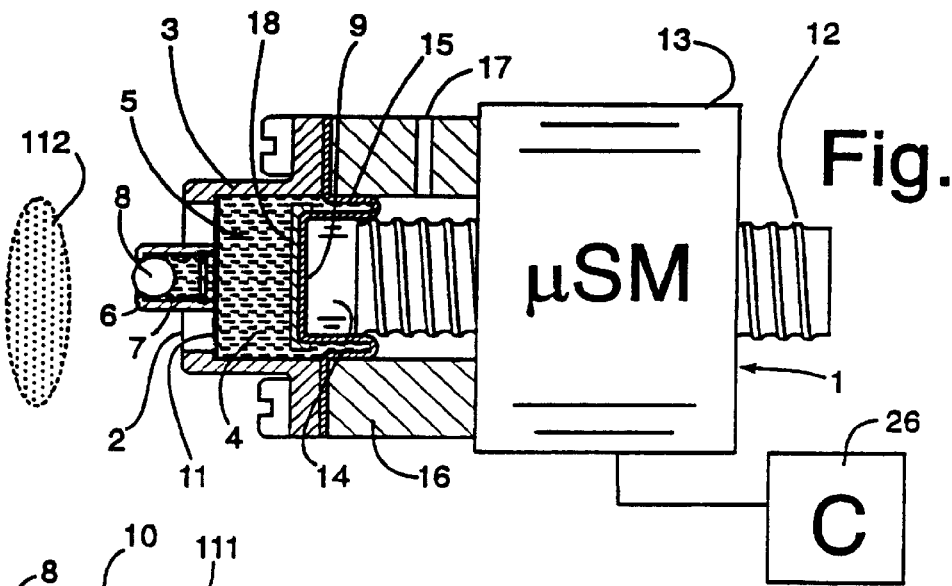
FIG. 1 is a partially sectioned side elevation of the aerosol generating and dispensing system of the invention.
Figure 2:
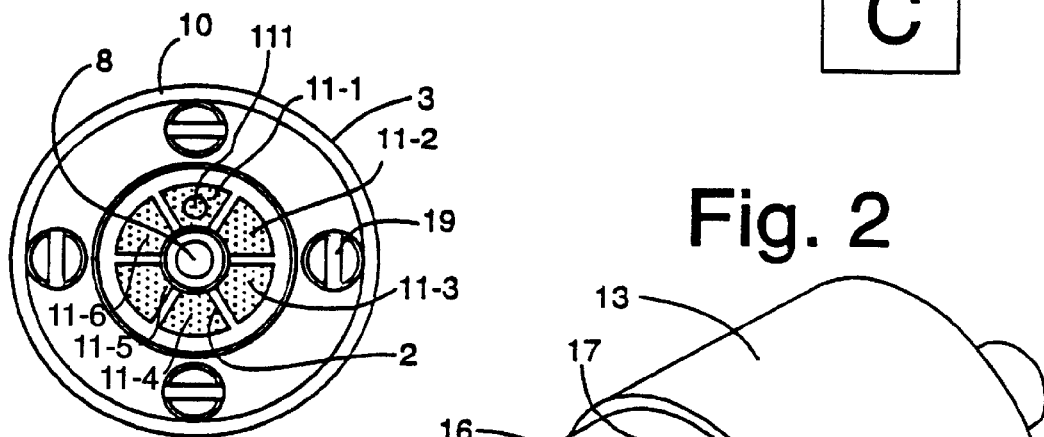
FIG. 2 is an isometric view of the aerosol generating and dispensing system of the invention.
Figure 3:
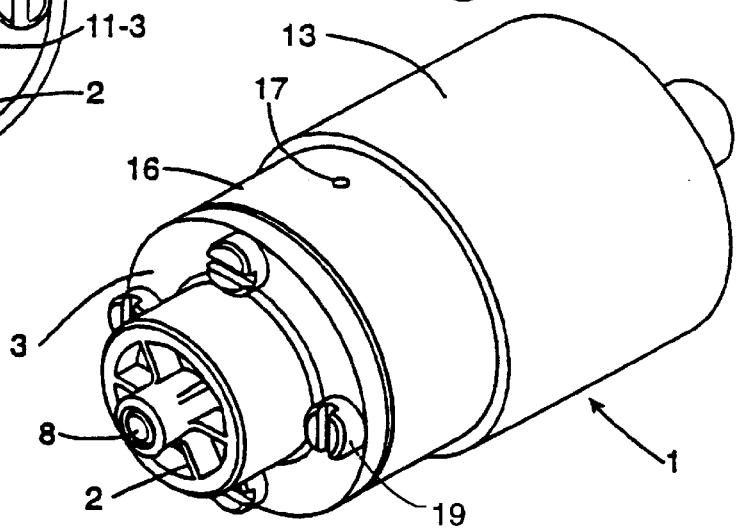
FIG. 3 is an end elevation view of the dispensing end of the aerosol generating and dispensing system of the invention.

FIG. 1 is a sectioned side elevation of the aerosol generating and dispensing system showing working details. FIGS. 2 and 3 show the external appearance. The following discussion will refer to these three figures as a group.

The function of the aerosol generating and dispensing system 1 of the invention is to generate mono-dispersed aerosol, by pulsing, so that for each pulse a precisely repeatable partial dose of liquid is delivered in aerosol form. Additionally, the pulse repetition rate is controllable to a high degree of accuracy to control the volume of liquid delivered. The aerosol generating and dispensing system 1 is valuable for use with pulmonary medications, for example, where an aerosol droplet diameter of 3-$\mu$m is optimal for medication delivery to the lungs. With this invention, it is possible to generate a liquid-originating aerosol from the system operating inherently in pulsed mode. Each pulse corresponds to a micro-step of the micro-stepper motor, at the required repetition rate, so that at every repetition a precise partial dose of a fixed number of individual 3-$\mu$m droplets of medication in aerosol form is emitted. Furthermore, by adjusting the repetition rate, it is possible to deliver highly accurate volumes of dose over precisely controlled intervals of time. Note that in the preferred method of operating this system, exactly one 3-$\mu$m droplet is ejected from every nozzle micro-via upon each pulse—thus the aggregate partial dose delivered, during any single pulse, is simply v=4/3 $\pi(1.5)^3$ $\mu m^3$ (i.e., the droplet volume of a 3-$\mu$m diameter droplet)*N (the total number of nozzles), and the dose quantity delivered per second is V*N*R, where R is the pulse repetition rate. Monodispersed-aerosol generating systems also would have a wide variety of applications in other areas, such as agriculture, spray coating, and military defense against biological weapons, to name a few.

As shown in FIGS. 1, 2 and 3, a six-section nozzle array 2 contained in via plate 11 is carried in a remountable housing 3, which holds the deliverable liquid medication 4 in a reservoir 5. In order to maintain the liquid medication 4 within the reservoir 5 within the remountable housing 3, the port window 6 (which serves as an inlet for filling the reservoir 5) is sealed by using a ball seal spring 7 to force the port seal ball 8 to seat firmly at the sealing edge of the port window 6. The rear of the reservoir 5 is sealed by the rolling diaphragm 9 (such as manufactured by Bellofram). The rolling diaphragm 9, the port seal ball 8, and the remountable housing 3, collectively, constitute the hermetic reservoir subassembly 10. The liquid medication 4 can exit from the reservoir 5 only by flowing through one or more of the nozzle micro-via sections 11-1 . . . 11-6 of the six-section nozzle array 2. The rolling diaphragm 9 maintains an intimate contact between its surface and the ball screw 12 at the operational end 14 of the ball screw 12 by means of retainer plate 18. The ball screw 12 is coupled to a high-precision variable-step micro-stepper motor 13 (such as from Oriental Motors, with up to 125,000 steps/revolution) which drives the ball screw 12 forward (0.254 cm./turn, as an example) toward the front of the reservoir 5 in a precise increment for each step, depending upon the step size selected. The design lends itself to fill and expel liquid medication 4 without air ingestion, thus, by ensuring that there are no air pockets within the reservoir 5, the forward motion of the ball screw 12 is directly coupled with the displaced liquid 4 within the reservoir 5. This results in a compressive force upon the liquid 4, forcing a finite volume of the liquid 4 out of the reservoir 5 through the micro-via-holes 111 in the nozzle array 2, forming a measured aerosol cloud shown schematically as aerosol cloud 112 in FIG. 1. After delivery of the finite volume of liquid 4, while the ball screw 12 is stationary, surface tension of the liquid prevents leakage of the fluid 4 through the nozzle micro-vias 111-1, 111-2 . . . 111-n in nozzle array micro-via plate 11. Note that due to the fold 15 present in the rolling diaphragm 9, the ball screw 12 is free to move without damaging the diaphragm seal. Additionally, note that when the reservoir 5 is initially filled free of any air pockets, it continues to maintain its freedom from air-pockets throughout the entire forward motion of the ball screw 12 because of the flexible but non-stretchable nature of the rolling diaphragm 9, which forces the fluid 4 in the reservoir 5 through the nozzle array 2 as the fluid 4 is subjected to compression forces.

Driven by the micro-stepper 13 under the control of control means 26, the ball screw 12 moves forward until the reservoir 5 (which can hold multiple doses of liquid medication) is nearly depleted. In order to refill the reservoir 5, the remountable housing 3 is immersed past via-plate 11 into a liquid bath containing the refill fluid and the port seal ball 8 is depressed, breaking the port window seal, and exposing the reservoir 5 volume to the liquid 4 within the bath. The micro-stepper 13 is then operated in reverse, moving the ball screw 12 backward, away from the port window 6. This motion, which creates a vacuum within the depleted reservoir 5, draws the refill fluid 4 into the reservoir 5.

One of the key aspects of this design is the pulsed nature in which the ball screw 12 is stepped forward. It is a characteristic of a continuous liquid stream that it breaks up into droplets under the influence of the surface tension of the fluid, and furthermore that there is a wide range of droplet sizes that may develop. This can be a problem with commercially available aerosol generators, such as those currently used for asthma therapy, with which the user depresses a plunger in a continuous motion. With the design of this invention, fluid is ejected in discrete unit-volume packets, rather than as a continuous stream. Furthermore, under optimized conditions, the forward increment of the ball screw 12 is precisely controlled such that exactly port window sufficient volume of liquid to form one droplet is ejected from every micro-via-hole upon each micro-step.

Details of the system include:

a micro-stepper 13 coupled to a ball screw;

a spacer 16 with its vent hole 17, which prevents the build up of pressure differentials as the ball screw is extended or retracted;

a retainer plate 18 which secures rolling diaphragm 9 hole in intimate contact with the end of the ball screw 12 to prevent the reversal of the diaphragm fold 15 at the extreme retracted position; and a set of screws 19 which hold the remountable housing 3, spacer 16 and micro-stepper 13 in place.

Figure 4:
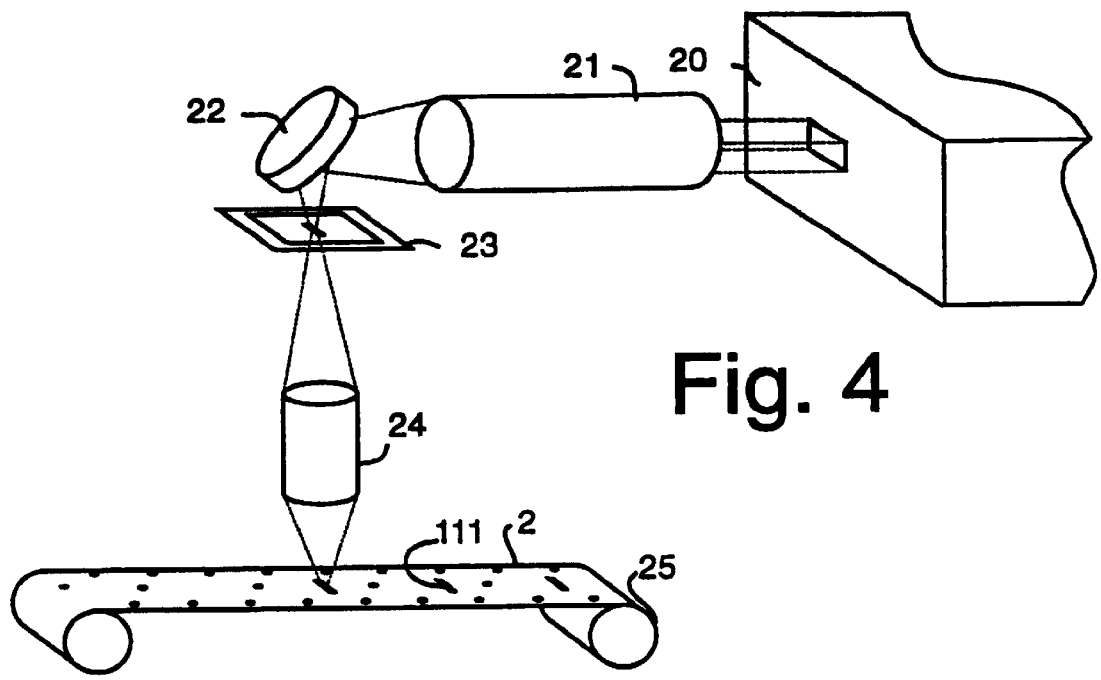
FIG. 4 is a diagram showing how the nozzle array is made, according to a previous, commonly assigned, patent application.

FIG. 4 generally describes the preferred prior art technique for making the nozzle array 2 according to a commonly assigned prior copending U.S. patent application Ser. No. 08/794,217, which has been allowed and the final fee paid.

Figure 5:
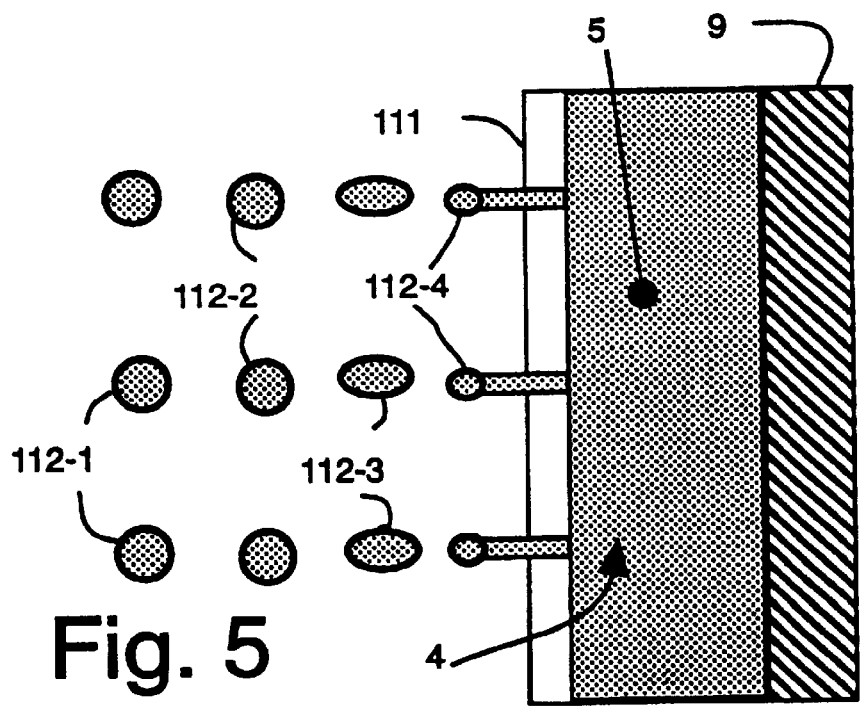
FIG. 5 is a semi-diagrammatic view showing micro-droplet formation, occurring as a result of surface tension, of liquid expelled during a sequence of four pulses from a set of micro-vias in the nozzle array.

FIG. 5 generally describes what happens when liquid jets, exiting the micro-vias 111 of multi-hole nozzle array 2, form into aerosol droplets 112-1 . . . 112-n, as a result of their pulsed origin and the sphere-forming characteristic of surface tension in the aerosol-forming liquid. FIG. 6 is a histogram of exit aperture sizes for the micro-vias 111 of the nozzle array 2, to prevent the reversal of the diaphragm fold 15 at the extreme retracted position expressed as number of apertures in % of total versus their size in microns, showing a mean size of 1.3 microns.

FIGS. 7–8 illustrate the characteristics of nozzle array 2, including imperfections in via-holes 111. The droplet formation shown in FIG. 5 occurs since the pulsed mechanism ejects the liquid in infinitesimally small, separated jet columns, which, under the influence of surface tension, form and maintain themselves as individual droplets. This is in contrast to many other aerosol generating systems which eject a continuous stream of fluid through a nozzle array. Thus, for example, with this invention where there are N nozzle array micro-via openings, there are N droplets generated upon each pulse. If the desired droplet diameter were 3-$\mu$m, then the total volume of fluid that would be ejected per pulse would be $N*4/3\pi$ $(1.5\ \mu m)^3 \sim 14\ N\ \mu m^3$. In order to achieve this total volume of aerosol generated per pulse it would be required only to increment the ball screw forward such that the forward motion reduces the volume of the reservoir by the same quantity, i.e., $14\ N\ \mu m^3$. Thus, under optimal conditions operating in pulsed mode, the droplet size can be precisely set by the controlling magnitude of the ball screw increment.

Evaluating typical design parameters will elucidate the previous discussion. Referring to FIGS. 2 and 3, the system consists of six (each 145,000-via-hole) nozzle arrays aggregating a total of ~870,000 1-$\mu$m-diameter holes over a total area A=2 cm$^2$. Thus, if each nozzle in each of the six nozzle arrays emitted sufficient volume for a 3-$\mu$m-diameter (volume ~14 $\mu m^3$) droplet upon each pulse, then the total volume of liquid ejected would be $\sim 1.2*10^7\ \mu m^3$ ($=1.2*10^{-5}$ cm$^3$, or $1.2*10^{-5}$ ml). As described in the previous paragraph, this is the volume of liquid displaced by the ball screw 12 for each step of the micro-stepper 13. Note that the volume of liquid displaced when the ball screw 12 moves forward is given simply by $A*d$, where A is the effective area of the rolling diaphragm 9 and d is the distance, or increment, that the ball screw 12 moves forward upon each step. The invention as implemented incorporates a rolling diaphragm 9 having an effective area of 0.97 cm$^2$ and a ball screw 12 coupled to a micro-stepper motor ($\mu$SM) 13, providing an incremental motion of ~0.13 $\mu$m ($=10^{-5}$ cm). This corresponds to a displaced fluid volume of $10^{-5}$ ml per pulse, which is the required amount, as calculated above. Note that the device is capable of delivering multiple doses of medication, depending upon the volume of the reservoir. As implemented, the invention has a total reservoir volume of 0.6 ml. It is important to note that by using a variable-step-size micro-stepper motor ($\mu$SM) 13, the droplet size can be varied by simply changing the step size to alter the incremental movement of the ball screw 12 upon each step.

The invention is simple in design, consisting of a small number of customized components—that can easily be designed for large-scale production—as well as readily available off-the-shelf components. For example, the values used to estimate the specifications of the micro-stepper motor ($\mu$SM) 13, ball screw 12 and rolling diaphragm 9 are all derived from commercially-available products. Note that the micro-stepper motor ($\mu$SM) 13 and ball screw 12 assembly have extremely long lifetimes, and if a new nozzle array 2 needs to be installed it is only necessary to remove the remountable housing 3, which with rolling diaphragm 9 defines the fluid reservoir 5, and replace the nozzle array 2 with a new nozzle array 2. Additionally, it is possible to switch a particular nozzle array 2 with a different nozzle array 2 having a different via-hole size, so that the same device can be used with a nozzle array optimized for some other application.

The reservoir housing subsystem is inexpensive to replace, and, since it is possible to manufacture the housing in large-scale production at a low cost by injection-molding, for example, it will be advisable at some finite level of production to integrate the nozzle array 2 by bonding it into a replaceable housing which can be manufactured cost-effectively.

Method

The method of generating an aerosol from a system having a fluid reservoir, a nozzle array at an aerosol delivery position with respect to said fluid reservoir and said nozzle array, and having a micro-stepper-operated linear actuator for altering the volume of the fluid reservoir in response to control pulses from a control means with a dosage counter characterized by the following steps:

Step 1) activating a micro-stepper (13) to provide motion to the linear actuator (12) which increases the volume of fluid (4) a fluid reservoir (5) having fill means (6–8) at an aerosol fluid acceptance position, so as to fill the reservoir (5) without air pockets;

Step 2) providing a control pulse for activating the micro-stepper (13) to provide motion to the linear actuator (12) which decrements the volume of the fluid reservoir (5), which is operatively mounted at an aerosol delivery position, said nozzle array (2) having a large finite number of operational micro-vias (111) of controlled characteristics related to selected droplet size, to deliver in aerosol form a finite volume of fluid (4); and Step 3) repeating Step 2 a finite number of repetitions of the control pulse according to the dosage counter.

Summary

The system generates a mono-dispersed aerosol, with droplet size precisely controlled by a micro-stepper motor and the micro-vias 111 of a nozzle array 2. Additionally, a specified dose can be delivered over an accurately controlled interval of time. The system is compact and simple in design; the motor/actuator components are readily available off-the-shelf items and have extremely long lifetimes. The system can be refilled after use, and the aerosol nozzle array 2, which is the component most likely to require replacement with extended use, can easily be replaced. The replacement of the nozzle array 2 is a simple procedure, and, additionally, new nozzle arrays are inexpensive since they can be manufactured at a low cost using laser lithographic technology in mass production.

What is claimed is:

1. A method of generating measured fluid in aerosol mode from a system having a fluid reservoir, a nozzle array at an aerosol delivery position with respect to said fluid reservoir and said nozzle array, and having a micro-stepper-operated linear actuator (12) for altering the volume of the fluid reservoir according to pulses from a control means having a dosage counter, characterized by the following steps:

Step 1) activating a micro-stepper (13) to provide motion to the linear actuator (12) which increases the volume of a fluid reservoir having fill means at an aerosol fluid acceptance position, so as to fill the reservoir without air pockets;

Step 2) providing a control pulse for activating the micro-stepper (13) to provide motion to the linear actuator (12) which decrements the volume of a fluid reservoir by a single unit volume per control pulse, said fluid reservoir being mounted at an aerosol delivery position, said nozzle array (2) having a large finite number of operational micro-vias of controlled characteristics related to selected droplet size, to deliver in aerosol form said single unit volume of fluid, one droplet per operational micro-via per control pulse; and Step 3) repeating Step 2 by providing a selected number of repetitions of the control pulse according to the dosage counter in the control means.

2. An aerosol generating and dispensing system characterized by
   a) a micro-stepper (13) having a linear actuator (12);
   b) reservoir housing means (3), having an aerosol delivery end and having a micro-stepper end mountable to said micro-stepper (13);
   c) nozzle array means (2) mountable at the aerosol delivery end of said reservoir housing means (3), said nozzle array means (2) having myriad micro-vias of controlled characteristics related to selected droplet size;
   d) reservoir housing means mounting means (16, 19) for mounting said reservoir housing means (3) to said micro-stepper (13), forming with said nozzle array means (2) a reservoir (5) that has its volume subject to change by said linear actuator (12) when moved by said micro-stepper (13); and
   e) micro-stepper control means (26) operatively connected to said micro-stepper (13); whereby each step of said micro-stepper (13) under control of said control means (26) which diminishes the volume of said reservoir (5) by a controlled amount expels an individual micro-droplet from each operational micro-via of said nozzle array means (2).

3. An aerosol generating and dispensing system according to claim 2, further characterized by diaphragm means (9) mounted between said linear actuator (12) and said reservoir housing means (3).

4. An aerosol generating and dispensing system according to claim 3, further characterized in that said diaphragm means (9) is a rolling diaphragm mounted between said linear actuator (12) and said reservoir housing means (3).

5. An aerosol generating and dispensing system according to claim 4, further characterized in that said linear actuator (12) has an operational end (14); and
   said diaphragm means (9) is a rolling diaphragm mounted between said linear actuator (12) operational end (14) and said reservoir housing means (3) and held by retainer plate clamp (18) to said operational end (14).

6. An aerosol generating and dispensing system according to claim 2, further characterized in that said nozzle array (2) comprises a large finite number of micro-via holes substantially on fifteen-micron centers with exit apertures closely arranged about a mean diameter of 1.5 microns.

7. An aerosol generating and dispensing system characterized by
   a) a rotary micro-stepper (13) having a linear ball screw actuator (12);
   b) reservoir housing means (3), having an aerosol delivery end and having a micro-stepper end mountable to said micro-stepper (13) through spacer means (16);
   c) nozzle array means (2) mountable at the aerosol delivery end of said reservoir housing means (3), said nozzle array means (2) having a large finite number of operational micro-vias of controlled characteristics related to selected droplet size;
   d) reservoir housing means mounting means (16, 19) for mounting said reservoir housing means (3) to said micro-stepper (13), forming with said nozzle array means (2) a reservoir (5) that has its volume subject to change by said linear actuator (12) when moved by said micro-stepper (13), and has fill-valve means (6, 8); and
   e) micro-stepper control means (26) operatively connected to said micro-stepper (13);
   whereby each step of said micro-stepper (13), under control of said control means (26) which diminishes the volume of said reservoir (5) by a controlled amount, expels an individual micro-droplet from each of said finite number of operational micro-vias of said nozzle array means (2).

* * * * *